United States Patent [19]

Kakimi et al.

[11] 4,342,739

[45] Aug. 3, 1982

[54] NOVEL MATERIAL FOR IMMUNOLOGICAL ASSAY OF BIOCHEMICAL COMPONENTS AND A PROCESS FOR THE DETERMINATION OF SAID COMPONENTS

[75] Inventors: Fujio Kakimi, Minami-ashigara; Nobuo Hiratsuka, Tokyo; Hiroharu Matsukawa, Shizuokashi, all of Japan

[73] Assignee: Fuji Photo Film Co., Ltd., Kanagawa, Japan

[21] Appl. No.: 110,318

[22] Filed: Jan. 8, 1980

[30] Foreign Application Priority Data

| | | |
|---|---|---|
| Jan. 9, 1979 [JP] | Japan | 54-1555 |
| Nov. 16, 1979 [JP] | Japan | 54-149209 |
| Nov. 16, 1979 [JP] | Japan | 54-149210 |

[51] Int. Cl.³ .................. G01N 33/58; G01N 33/60; B01J 13/02
[52] U.S. Cl. ..................... 424/1; 23/230 B; 252/316; 424/12; 424/32
[58] Field of Search .............. 424/1, 12, 32; 23/230 B; 252/316

[56] References Cited

U.S. PATENT DOCUMENTS

| | | | |
|---|---|---|---|
| 3,853,987 | 12/1974 | Dreyer | 424/1 |
| 4,021,364 | 5/1977 | Speiser et al. | 424/1 |
| 4,061,466 | 12/1977 | Sjöholm et al. | 424/1.5 |
| 4,108,975 | 8/1978 | Hales | 424/1 |
| 4,115,534 | 9/1978 | Ithakissios | 424/1 |
| 4,115,535 | 9/1978 | Giaever | 424/1 |
| 4,166,102 | 8/1979 | Johnson | 424/1 |
| 4,177,253 | 12/1979 | Davies | 424/1 |
| 4,225,574 | 9/1980 | Romelli et al. | 424/1 |
| 4,235,865 | 11/1980 | Thoma | 424/1 |

OTHER PUBLICATIONS

Ashkar et al., Chemical Abstracts, vol. 91, 1979, Abstract #189177f.
Buehler et al., Clin. Chem., vol. 24, No. 6, 1978, p. 1040.

*Primary Examiner*—Christine M. Nucker
*Attorney, Agent, or Firm*—Sughrue, Mion, Zinn, Macpeak & Seas

[57] ABSTRACT

Antigen- or antibody-bound microcapsules are employed for immunological assay of biochemical components having immunological activity. The microcapsule system provides high detection sensitivity, high accuracy and excellent reproducibility in immunological assay, without causing non-specific reaction. The microcapsules can be labelled with isotopes, enzymes, etc., for use in quantitative assays of trace amounts of biochemical components.

37 Claims, No Drawings

NOVEL MATERIAL FOR IMMUNOLOGICAL ASSAY OF BIOCHEMICAL COMPONENTS AND A PROCESS FOR THE DETERMINATION OF SAID COMPONENTS

BACKGROUND OF THE INVENTION

1. Field of the Invention

The present invention relates to microcapsules for the immunological determination of trace amounts of biochemical components utilizing immunological reaction which comprise a core material and a wall material having an antigen or antibody bound thereto on the surface thereof.

The present invention also relates to a process for the determination of such biochemical components using such microcapsules.

2. Brief Description of the Prior Art

Various methods have been proposed for the immunological determination of biochemical components having immunological activity. For example, one known method relates to determining biochemical components by observing agglutination between test samples and antigen- or antibody-coupled animal blood red cell (also referred to as erythrocyte), a high molecular weight latex, high molecular weight polymer particles, etc., on a microplate or the like. In recent years, the art has also directed substantial attention to radioimmunoassay and enzyme immunoassay.

In the prior art methods, while sheep blood red cell is most commonly used as a carrier particle for binding an antigen or antibody used in the agglutination of an antigen-antibody reaction, organic or inorganic particles such as a polystyrene latex, a polyester, a nylon, kaolin, etc., have also been employed. In the case of using such carrier particles, blood red cells have been coupled with an antigen or antibody using an aldehyde such as glutaraldehyde, etc., while a polystyrene latex, a polyester, a nylon, kaolin, etc., have been physically bound thereto utilizing physical adsorption.

However, in the case of using sheep red cells as carrier particles, quality was uneven and the antigen-antibody reaction has been interpreted only with poor accuracy since these carrier particles originate from a living body. Furthermore, non-specific reactions tend to occur since the sheep red cell carrier inherently has antigens and antibodies, reproducibility of the antigen-antibody reaction is poor and cost is high, all of which are disadvantages in using sheep red cells as carrier particles.

On the other hand, systems using a polystyrene latex, a polyester, a nylon, inorganic particles or the like encounter other shortcomings, e.g., in addition to high cost, immobilization is weak due to physical adsorption of the antigen or antibody to the carrier particles and, as a result, an antigen or antibody is not easy to isolate, sensitivity of the antigen-antibody reaction is reduced and reproducibility of the antigen-antibody reaction is inferior. These disadvantages increase dramatically when the analytical system is stored for a long period of time.

SUMMARY OF THE INVENTION

One object of the present invention is to provide microcapsules for the immunological determination of biochemical components which overcome the above disadvantages of the prior art.

A further object of the present invention is to provide a process for the immunological determination of biochemical components using such microcapsules.

In the present invention, the term "bind, binding or bound" refers to the state of binding an antigen or antibody directly or indirectly to the surface of a wall material of a microcapsule in the broad sense. As far as such antigen- or antibody- "bound" microcapsules effectively cause an immunological response or reaction, it is not important how such "bound" microcapsules are formed.

However, as is generally understood in this art, an antigen or antibody is "bound" to a microcapsule wall by cross-linking, covalent binding or coupling. The term "bind, binding or bound" used in the present specification is meant to include each of these cases.

The term "antigen" is established in the immunological art and can also be phrased as lipids, proteins, glucoses and complexes thereof (e.g., glucoproteins, lipoproteins, glucolipids), hormones, vitamines, etc. having immunogenicity.

The term "antibody" is also established in the art and no further explanation is believed needed. An antibody is also called immunoglobulin collectively.

DETAILED DESCRIPTION OF THE INVENTION

According to the present invention, a trace amount of components contained in a sample to be examined can be detected easily and accurately in a simple manner.

The microcapsules which can be employed in the present invention comprise a core material and a wall material having an antigen or antibody bound to the surface of the wall material.

To bind an antigen or antibody to a microcapsule, various conventional methods can be employed, e.g., an aldehyde cross-linking method, an alkylation method, a cyan bromide method, a carbodiimide cross-linking method, an isocyanate cross-linking method, a maleimide cross-linking method, a benzophenone cross-linking method, a periodic acid cross-linking method, etc., details of which are given in Ichiro Chihata, *KOTEIKA KOSO* (Immobilized Enzyme), Kodansha Publishing Co., Ltd. (1975) and Eiji Ishikawa, *KOSO MENEKI SOKUTEIHO* (Enzyme Immunoassay), pages 34 to 44. While binding method(s) selected is/are not limitative, it is important that the antigens or antibodies bound should not be inactivated.

The most typical method is binding using an aldehyde such as glutaraldehyde, formaldehyde, glyoxal, etc. According to this method, the microcapsules are mixed with about 0.2 to about 2% of, e.g., glutaraldehyde at temperatures of about 15° to about 40° C., preferably ambient temperature, for about 1 to about 2 hrs., under normal pressure, and the mixture is washed with distilled water to remove the unreacted aldehyde. Then, the glutaraldehyde-treated microcapsules are mixed with about 0.1 to about 5% antigen or antibody, followed by reaction at room temperature for 1 to 2 hrs. The binding or cross-linking agents are not limited to aldehydes and additional representative materials include toluene-2,4-diisocyanate, N,N',O-phenylenedimaleimide, m-maleimidobenzoyl, N-hydroxysuccinimide, etc.

In order to check if the bond could be formed between microcapsules and antigen or antibody, a simple test is generally performed utilizing an immunofluorescence technique (*A Dictionary of Immunology*, pages 128 and 129, (1979), published by Hirokawa Publishing Co., Tokyo) which comprises binding a fluorochrome with an antibody and mixing the fluorochrome-labelled antibody with microcapsules that would be bound to the antigen and then measuring the fluorochrome after washing the mixture with water. If the fluorochrome can be detected, it is judged that the microcapsule-antigen bond would be formed.

When antigens or antibodies are bound to microcapsules, it is necessary to suitably choose the composition of the microcapsule walls depending upon the combination of the antigens or antibodies and the walls. For example, in binding antigens or antibodies to microcapsules walls using aldehydes, it is advantageous that active proton containing materials, e.g., containing amino, imino, hydroxy, etc., groups be present in the microcapsule walls. One skilled in the art will be able to determine which combination is suitable for binding any particular antigen or antibody to a microcapsule wall and no further explanation is believed needed.

The wall material of the microcapsules in the present invention are not limited so long as the wall material can bind to antigens or antibodies without inactivating antigens and antibodies and, of course, wall materials include materials having an amino, imino, hydroxy, sulfhydryl group, etc., e.g., proteins (e.g., collagen, gelatin, casein, etc.); resins such as polyamino acids, polyacrylamide, polyamide, polyurethane, polyurea, polyurethane-urea, melamine resin, phenol resin, epoxy resin, silicone resin and derivatives thereof; cellulose and derivatives thereof (e.g., methyl cellulose, ethyl cellulose, carboxymethyl cellulose, nitrocellulose, cellulose acetate, cellulose sulfate, etc.), gum arabic, starch, aliginic acid, and the like.

While not limitative, it is desired that an average diameter of microcapsules be ranging from about 0.1 to about 30 microns, preferably 0.5 to 10 microns.

Details on various wall materials and methods for the microencapsulation thereof as can be used in the present invention are described in, e.g., Asaji Kondo, *MICROCAPSULE*, Nikkan Kogyo Press, Tokyo (1970), Tamotsu Kondo and Masumi Koishi, *MICROCAPSULE*, Sankyo Publishing Co., Ltd., Tokyo (1972), etc., and hereby incorporated by reference.

In a manner similar to the wall materials, useful core materials are not unduly limited. Typical examples of oily substances which can be used as core materials include natural mineral oils, animal oils, plant oils and synthetic oils.

Examples of useful mineral oils include petroleum, kerosene, gasoline, naphtha, paraffin oil, etc.; useful animal oils include fish oil, lard, etc.; and useful plant oils include peanut oil, linseed oil, soybean oil, castor oil, corn oil, etc.; useful synthetic oils include biphenyl compounds (e.g., isopropyl biphenyl, isoamyl biphenyl), terphenyl compound (e.g., see West German OLS 2,153,635), naphthalene compounds (e.g., diisopropylnaphthalene and materials as disclosed in U.S. Pat. No. 4,003,589), alkylated diphenylalkanes (e.g., 2,4-dimethyldiphenylmethane and materials as disclosed in U.S. Pat. No. 3,836,383), phthalic acid compounds (e.g., diethyl phthalate, dibutyl phthalate, dioctyl phthalate), etc.

The core material encapsuled in the microcapsules of the present invention is not limited to the substances described above.

To improve contrast in the case of using microcapsules in agglutination, oleophilic coloring dyes can be incorporated in the core material. While the coloring dyes are not limited, examples thereof include Color Index Solvent Red 1, 3, 8, 23, 24, 25, 27, 30, 49, 81, 82, 83, 84, 100, 109 and 121; Color Index Solvent Violet 8, 13, 14, 21 and 27; Color Index Solvent Blue 2, 11, 12, 25, 35, 36, 55 and 73; Color Index Solvent Green 3; Color Index Solvent Brown 3, 5, 20 and 37; Color Index Solvent Black 3, 5, 7, 22, 23 and 123, etc.

Though it is possible to color carrier particles to improve contrast, particularly in antigen-antibody agglutination in the case of using, e.g., a polystyrene latex, a polyester, a nylon, etc., dyes which are available are extremely limited in these cases since there is an increased possibility that a dye might adversely affect the antigen-antibody reaction. Thus, the choice of a suitable dye is made only with extensive research. In addition, high production cost is involved.

On the other hand, in the case of using microcapsules as carrier particles, it is effective to merely incorporate the dye(s) into the core material, whereby there is no chance of causing adverse affects on antigen-antibody reaction. Thus, it is possible to choose dyes only from the viewpoint of improving contrast and reducing cost since the capsule wall material serves as an effective barrier.

Furthermore, specific gravity and particle size cannot be controlled using sheep red blood cells since such is natural substance, nor is such easily controlled using a polystyrene latex, a polyester, a nylon, an inorganic particle, etc. However, in the case of using microcapsules as carrier particles, specific gravity can easily be controlled by mixing two kinds of core materials having different specific gravities, or dispersing inactive solid particles in the core material, etc., in a manner known in the microcapsule formation art. In the case of using microcapsules, particle size can also be easily controlled. For these reasons, the use of microcapsules as carrier particles is highly advantageous.

From viewpoints of obtaining an immediate antigen-antibody response and improving sensitivity, it is preferred that the specific gravity of microcapsules used in the present invention range from about 0.8 to about 1.20. When the specific gravity range is between 1.05 and 1.20, most preferably 1.07 and 1.16, such a system can be most advantageously used in antigen or antibody measurement by a microtiter method (a passive agglutination method using a microplate). Further, when microcapsules having a specific gravity between about 1.11 and about 1.15 are utilized, not only is the time period necessary for sample judgement, i.e., the time period until a difference appears on the microplate between a positive pattern and a negative pattern (which is referred to as "judgement time" herein) markedly shortened, but also a positive or negative pattern appears extremely clearly.

In addition, when the specific gravity of microcapsules approximates 0.8, agglutination can easily be performed using whole blood without separating red cells from the whole blood.

Further, as compared to the prior art system using sheep red blood cells as carrier particles, the microcapsule system of the present invention does not result in undesired non-specific reactions which are unavoidably observed in the case of using naturally occurring sheep red blood cells. Also, the microcapsule systems of the present invention can be stored for long periods of time without loss of effectiveness.

The microcapsule systems according to the present invention can be utilized in a wide variety of immunological examinations and this use is further extended to a variety of areas when the microcapsule system is labelled with one or more marking substances For example, the microcapsule system of the present invention can be used in radioimmunoassay which comprises determining an unknown substance and a microcapsule system labelled with a radioisotope such as $^{125}$I, $^{131}$I, $^{3}$H, $^{14}$C, etc. (details are given in Kumahara and Shizume, *Shinpan Radioimmunoassay*, pages 3–10, 1977, published by Asakura Shoten, Tokyo, etc., hereby incorporated by reference). Marking substances useful to determine unknown substances are illustrated below.

Marking substances advantageously employed in the present invention include, e.g., isotopes, enzymes, fluorescent substances, magnetic substances, ultraviolet absorbents, dyes, etc. These marking substances are employed in a conventional fashion dependent upon type of unknown substance to be determined, the method of determination thereof, etc. Of these marking substances, substances other than isotopes are preferred in view of problems such as waste matter treatment, operational safety and marking substance storability. In addition, such substances provide higher detection sensitivity and lower cost can be used in a simpler manner than in the case of using isotopes.

These marking substances can be bound to the outside (surface) of the wall material of a microcapsule or can be incorporated into the core material thereof. When a marking substance is incorporated (or dispersed) into the core material, there is great latitude in choosing the marking substance and content thereof, and one can freely select an appropriate marking substances depending upon the purpose involved.

In addition, immunological reaction proceeds without interference since the marking substances do not come into direct contact with an antigen or antibody, being separated therefrom by the microcapsule wall. For instance, enzyme immunoassay has heretofore been subject to the problems that storability and stability of the enzymes are poor when a marking substance and its method per se is unsatisfactory in accuracy and reproducibility. However, in the case of using an enzyme incorporated into the core material of a microcapsule system of the present invention, which consists of an aqueous solution, the disadvantages encountered in the prior art can be overcome.

As a representative of methods of directly labelling antigens or antibodies with a fluorescent substance, using FITC [Anami, et al., *KISO SEIKAGAKU JIKKENHO* (Basic Biochemical Experiment), vol. 6, page 167 (1976), Maruzen Publishing Co., Ltd. Tokyo] is known. However, according to this method, the amount of fluorescent substance to be labelled to molecules of antigens or antibodies is limited so as not to inhibit immune reaction. Therefore, in order to further enhance sensitivity, it is preferred that the fluorescent substance be incorporated into the core material. In this embodiment, marking substances can be used in an amount as required in proportion to the detection sensitivity required so that extremely high marking intensity can be obtained and hence detection sensitivity markedly enhanced. Measurement of trace amounts of antigens or antibodies contained in a sample can be made by binding antigens or antibodies corresponding to components in the sample onto the surface of microcapsules having incorporated therein, e.g., a fluorescent substance, causing an immune reaction between the microcapsules and the antigens or antibodies contained in the sample, either directly or indirectly, and then separating the antigen-ant body reaction product from the unreacted antigens or antibodies and determining an amount of fluorescent substance (degree of fluorescene) contained in the microcapsules. In a marking substances are microencapsulated as a core material as described above, material for immunological assay use having improved stability, accuracy and reproducibility and high sensitivity are obtained due to the excellent uniformity of the core material and the improved coating ability of the wall material.

Further, the microcapsules of the present invention can be used as carriers for immunological response. For example, use as carriers for enzyme immunoassay (see E. Ishikawa, *Enzyme Immunoassay*, 1978, Igakushoin Publishing Co., Ltd., Tokyo) and radioimmunoassay (*A Dictionary of Immunology*, page 290 (1979), Hirokawa Shoten, Tokyo) are representative examples thereof.

Furthermore, the microcapsules of the present invention can be employed instead of blood cells such as erythrocytes, leucocytes, lymphotcytes, or galss beads as are conventionally used for determining biological components contained in a sample.

Typical examples of radioisotopes include $^{125}$I, $^{131}$I, $^{3}$H, $^{14}$C, etc. The amount of isotopes to be labelled varies depending upon kind of the microcapsule system used, antigen or antibody, etc. and is not generally limited to a specific range; however, isotopes having an intensity of 100 mci/ml are generally used and are effective in achieving marking purposes.

Typical examples of fluorescent marking substances which can be used in the present invention include stilbene and derivatives thereof (e.g., 4,4'-diaminostilbene derivatives, 4,4'-diaminostilbene disulfonic acid derivatives, aminostilbene-2,2'-disulfonic acid derivatives, etc.), coumarine derivatives, benzoxazole derivatives, bisoxazole, pyrazoline derivatives, 4,4'-bistriazinyl, etc., are exemplified by the following compounds.

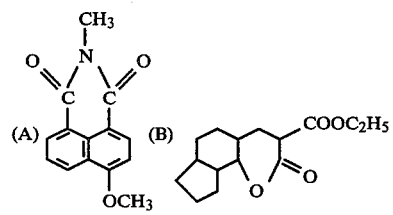

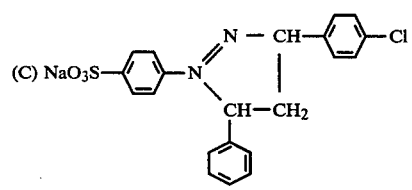

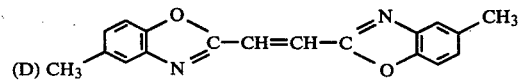

(E) 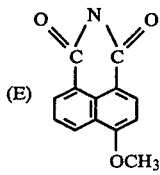

(F) 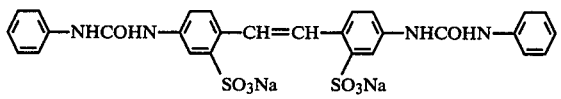

Specific examples of enzymes which can be employed as marking substances in the present invention include alkali phosphatase, β-galactosidase, acetylcholine esterase, glucoamilase, maleic acid dehydrogenase, glucose-6-phosphoric acid dehydrogenase, peroxidase, glutaroxidase, etc.

Specific examples of magnetic substances which can be employed as marking substances in the present invention include iron powders, nickel, cobalt, $CrO_2$, CoO, NiO, $Mn_2O_3$, magnetic zinc oxides, magnetic iron oxides such as $MnFe_2O_4$ powder, $Fe_3O_4$ powders, $CoFe_2O_4$ powder, $NiFe_2O_4$ powder, $CuFe_2O_4$ powder, $MgFe_2O_4$ powder, etc.; alloys of Al, Ni, Co, Cu, etc.; non-crystalline substances having magnetic property such as chalcogenides, ferricolloid powders, etc.

Specific examples of UV absorbents which can be employed as marking substances in the present invention include salicylic acid derivatives, e.g., phenyl salicylate, 4-t-butylphenyl salicylate, bisphenyl A-disalicylate, etc.; benzophenone derivatives, e.g., 2-hydroxy-4-methoxybenzophenone, 2-hydroxy-4-methoxy-2'-carboxybenzophenone, 2-hydroxy-4-octoxybenzophenone, 2-hydroxy-4-octoxybenzophenone, 2-hydroxy-4-stearyloxybenzophenone, 4-dodecyloxy-2-hydroxybenzophenone, 2-hydroxy-4-methoxy-5-sulfobenzophenone trihydrate, 2-hydroxy-4-methoxybenzophenone-5-sulfonic acid, 2-hydroxy-4-(2-hydroxy-3-methacryloxy)-propoxybenzophenone, 2-hydroxy-4-methoxy-4'-methylbenzophenone, 2-hydroxy-4-benzoyloxybenzophenone, 2,4-dihydroxybenzophenone, 2,2'-dihydroxy-4-methoxybenzophenone, 2,2'-dihydroxy-4-n-octoxybenzophenone, methyl o-benzoylbenzoate, 2,2',4,4'-tetrahydroxybenzophenone, etc.; benzotriazole derivatives such as 2-(2'-hydroxy-5'-methylphenyl)benzotriazole, 2-(2'-hydroxy-3'-t-butyl-5'-methylphenyl)-5-chlorobenzotriazole, 2-(2'-hydroxy-3',5'-di-t-butylphenyl)-5-chlorobenzotriazole, 2-(2'-hydroxy-3',5'-dibenzylphenyl)-benzotriazole, 2-(2'-hydroxy-4'-octoxyphenylbenzotriazole, etc.

In the present invention, dyes can also be employed as markers. Typical examples of such dyes as those previously exemplified for use in incorporating into the core material for the purpose of coloring the microcapsules.

In quantitatively determining the labelled substance, a suitable method or means dependent on the marking substance employed is chosen.

For example, when using a fluorescent marking substance, a degree of fluorescene is determined using a fluorophotometer, fluoropolarization photometer, etc.

When using a magnetic marking substance, electromagnetic properties can be measured to determine the labelled substance.

Further when using a UV absorbent, a quantitative determination can be made with a spectrometer.

In measuring turbidity or transmittance, or for a qualitative determination of the marking substances, a laser can be advantageously employed.

It is general that prior to the quantitative determination, the microcapsules are mechanically mashed as a pre-treatment.

The amount of the markers to be used are generally between about 0.1 and about 10 wt% based on the core material used, preferably 0.5 to 5 wt% when fluorescent substances, magnetic substances, UV absorbents and dyes are used as the markers. When enzymes are used, the amount is generally between about $10^{-2}$ and $10^{-10}$ mole per 1 g. of the core material, preferably $10^{-6}$ to $10^{-10}$ mole.

In one preferred embodiment of the present invention, the marking substance(s) is/are microencapsulated as a core material so that the marking substances are not affected by substances present outside the microcapsule walls. In addition, any adverse influence due to various conditions outside the microcapsule walls, e.g., pH or temperature, can be prevented. Accuracy can also be improved in a qualitative assay due to uniform and accurate encapsulation of the marking substances in the microcapsules. Encapsulation of the marking substances in the microcapsules in the amount required results in marked enhancement of detection sensitivity.

The antigen- or antibody-bound microcapsules of the present invention can be utilized in various immunological reactions.

Firstly, the microcapsule system can be effectively utilized in agglutination, more specificatlly, in the well known glass plate method (antigen- or antibody-bound microcapsules are mixed with a sample to be examined onto a glass plate; biological components can be detected whether or not agglutination occurs), in the well known method (often referred to as a microtiter method; double serial diluents of a sample to be examined are charged into a V- or U-shape tube having a diameter of about 5 m/m and the antigen- or antibody-bound microcapsules are dropped thereon; a qualitative assay can be performed by determining the concentration at which agglutination occurs; M. Kaneizume, *RINSHO KENSA TEIYO* (Outline of Clinical Test), vol. xx, page 10, Kanehara Publishing Co., Ltd. (1978) hereby incorporated by reference.).

In the present invention, the antigen-antibody reaction is carried out in conventional manner, e.g., by an direct antibody method, a direct antigen method, an indirect antibody method, a sandwich method, an indirect complement method, a direct complement method, etc., details of which are given in Anami and Miller, *KISO SEIKAGAKU JIKKENHO* (Basic Biochemical Experiment), vol. 6, page 167 (1976), Maruzen Publishing Co., Ltd., Tokyo.

Biological components which can be determined according to the present invention are, e.g., peptide hormones such as hypothalamus hormones (e.g., TRH, LH-RH, somatostatin), hypophysis hormones (e.g., growth hormone, ACTH, α-MSH, β-MSH, lipotropin, prolactin, TSH, TSH-β, LH, LH-β, FSH, FSH-β, α-subunit, arginine vasopressin, lysine vasopressin, oxytocin, etc.), calcium metabolism regulating hormones (e.g, insulin, proinsulin, C-peptide, glucagon, etc.), digestive tract hormones (e.g., gastrin, secretin, pancreozymincholecystokinin, GIP, enteroglucagon, etc.), hormones acting on blood vessels (e.g., angiotensin I, angiotensin II, bradykinins, etc.), placenta hormones (e.g., human chorionic gonadotropin(HCG), HCG-β, human chorionic somatomammotropin, human chorionic thyrotropin; non-peptide hormones such as steroids (e.g., cortisol, corticosterone, 11-deoxycortisol, 11-deoxycorticosterone, progesterone, 17-hydroxyprogesterone, pregnenolone, aldosterone, testosterone, dihydrotestosterone, estradiol, estriol, estrone, 2-hydroxyestrone, dehydroepiandrosterone, medroxyprogesterone, etc.), thyroid hormones (e.g., thyroxine, 3,5,3'-triiodothyronine, 3,3'5'-triiodothyronine, etc.), prostaglandins (e.g., prostaglandin A, E, F, etc.); substances other than hormones such as drugs (e.g., digoxin, digitoxin, morphine, LSD, gentamycin, amphetamine, nicotine, cotinine, etc.), cyclic nucleotides (e.g., cyclic AMP, cyclic GMP, cyclic IMP, cyclic UMP, etc.), enzymes (e.g., $C_1$ esterase, fructose 1,6-diphosphatase, alkaline phosphatase, dopamine beta hydroxylase, pepsinogen, etc.), virus specific antigens (e.g., hepatitis B virus, murine sarcomaleukemia virus, wooly monkey leukemia virus, avian tumor virus, plant virus, avian C-type virus, etc.), tumor antigens (e.g., α-fetoprotein, carinoembryonic antigen(CEA), etc.), blood serum proteins (e.g., thyroxine binding globulin(TBG), IgG, IgM, IgE, IgA, $α_2$-microglobulin, properdin, anti-Rh antibodies, transferrin, aplipoprotein, fibrinogen degradation products, antihemolytic factor, renin, etc.); rheumatism factor, folic acid, neurophysin, somatomedin B, nerve growth factor, epidermal growth factor, staphylococcal enterotoxin A and B, type A toxin of clostridium botulinum, myosin, encephalitogenic basic proteins, substance P, serotonin, conjugated cholyl bile acid, $H_B$s-antigen, etc. Needless to say, the biological components which can be determined in accordance with the present invention are not limited thereto.

Of these biological components, those which can be particularly preferably determined according to the invention are IgG, IgM, IgE, IgA, insulin, $H_B$-antigen, α-fetoprotein, human growth hormone, renin, gastrine, LH, FSH, cortisol, antiotensin, ACTH, C-peptide, CEA, glucagone, and aldosterone. According to the present invention, it is sufficient for determination of biological components that the content of the biological component(s) be $10^{-9}$ g/ml or more in the sample examined.

The following examples are to be taken as illustrative of current preferred modes of practicing the invention as not as limitative, unless otherwise indicated.

Further, unless otherwise indicated, all parts, percents, and the like are by weight and all processing was at ambient temperature, i.e., on the order of 20° to 30° C., and a phosphoric acid buffer solution has the same composition as used in Example 1.

EXAMPLE 1

Into 40 parts of water at 40° C., 5 parts of acid-treated gelatin having an isoelectric point of 7.8 and 5 parts of gum arabic were dissolved. While vigorously stirring, 50 parts of a diisopropylnaphthalene/chlorinated paraffin oil (chlorination degree 50%) mixture ratio=23.6:26.4) having a specific gravity of 1.10 and containing 1% of a dye of formula:

were added to the solution to obtain an O/W emulsion having an average droplet size of 6.0μ. Thereafter, the emulsion was diluted by adding 213 parts of warm water at 40° C. thereto. Glacial acetic acid was then dropwise added to the emulsion at a fixed rate with stirring to reduce the pH of the system to 4.6 and thereby cause coacervation.

After the system was cooled to 10° C. to gel the coacervate, the system was hardened by the addition of 2 parts of 37% formaldehyde. Then, 40 parts of a 10% aqueous solution of carboxymethyl cellulose (average polymerization degree; 220) were added to the system. In order to enhance the hardening effect, a 10% aqueous sodium hydroxide solution was dropwise added to adjust the pH to 10. The temperature of the system was then raised to 50° C. The thus prepared microcapsules were washed with water and filtered to remove remaining formaldehyde. The microcapsules had a specific gravity of 1.10 and an average particle size of 6.3 microns.

The thus obtained microcapsules were then washed with a phosphoric acid buffer (an aqueous solution obtained by dissolving 8 g. of NaCl, 0.2 g. of KCl, 2.9 g. of $Na_2HPO_4.12H_2O$ and 0.2 g. of $KH_2PO_4$ in water to make 1 liter), and 0.5 g. of the microcapsules then dispersed in 5 ml. of a fresh phosphoric acid buffer having the same composition as above.

To the resulting dispersion, 1 ml. of egg albumin (10 mg of egg albumin/ml) was added as antigen, whereafter 100 μl of a 25% aqueous glutaraldehyde solution was added to the resulting mixture.

The mixture was then reacted for 1 hr. at room temperature. Thereafter, the resulting reaction mixture was centrifuged and washed with fresh phosphoric acid buffer, and 0.5 g. of the resulting microcapsules were taken and again dispersed in 5 ml. of fresh phosphoric acid buffer. The buffer solution containing 1% of the antigen-bound microcapsules were thus obtained (Sample #1).

One drop (25 μl) of a fresh phosphoric acid buffer solution was then dropped using a dopper into each well of the first and second lines on a microplate having 12 wells×2 lines; whereafter 25 μl of rabbit antisera to the egg albumin was taken with a diluter and added to the dilution liquid (the phosphoric acid buffer dropped into the 12 wells) on the first line to form ½ dilution. After stirring, 25 μl was taken from the resulting first diluent well and added to the second well on the first line followed by stirring to form ¼ dilution. Again, 25 μl was taken from the resulting second diluent well and added to the third on the first line followed by stirring to form ⅛ dilution. This procedure was repeated until $2^{12}$ (4096) time diluents were obtained.

Nextly, 25 μl of the phospholic acid buffer containing 1% of the antigen-bound microcapsules was dropped with a dropper into the antiserum diluents in every line.

The microplate was then thoroughly shaken. After the antigen was well mixed with the antisera, the microplate was allowed to stand for 3 hrs. at room temperature.

Thereafter, the resulting precipitating patterns were read to interprete the results as positive or negative. In this evaluation, diagnosis was positive when microcapsule particles were spread over the entire portion of a sample examined due to agglutination and negative when the microcapsule particles were naturally precipitated at the center of the bottom of the well of the sample examined.

For purpose of comparison, commercially available red blood cells from a sheep were treated in a similar fashion and egg albumin was likewise bound to the so treated red blood cells as an antigen. Positive or negative interpretation was made as described above.

For purpose of further comparison, a polystyrene latex having an average particle size of 0.8μ and a specific gravity of 1.05 was treated in a similar fashion and egg albumin likewise bound to the so treated polystyrene latex as an antigen. Positive or negative interpretation was made as described above.

Each of the above runs were performed 10 times. The results showed that, in the case of using sheep red blood cells, agglutination sensitivity was equal to the case of using microcapsules but non-specific reaction was noted in 2 out of 10 cases; in the case of using the polystyrene latex, non-specific reaction was not noted but agglutination sensitivity was 1/16 that in the case of using microcapsules. On the other hand, no non-specific reaction was noted in the case of using microcapsules.

As can be understood from the above results, the system of the present invention using microcapsules as carrier particles provides high agglutination sensitivity due to the strong binding capability of the microcapsules to the antigen, and does not cause non-specific reactions as do sheep red blood cells, due to the inherent absence of antigens or antibodies therein, whereby reproducibility is markedly high.

EXAMPLE 2

In a manner similar to Example 1, i.e., using the same microcapsules and procedure, etc., RA-factor was measured except that modified human γ-globulin was used as an antigen. The experimental routine was performed in each instance with 10 repititions.

The results showed that in the case of using sheep red blood cells agglutination sensitivity was equal to that in the case of using the microcapsules of the invention but non-specific reaction was noted in 3 out of 10 cases; in the case of using the polystyrene latex, non-specific reaction was not noted, but agglutination sensitivity was reduced to ⅛ that of the microcapsules; non-specific reaction was not noted in the case of using the microcapsules.

It can thus be understood that using microcapsules as carrier particles provides high agglutination sensitivity due to the strong binding capability of the antigen to the microcapsules, no non-specific reaction is caused due to the inherent absence of any antibody or antigen, unlike sheep red blood cells, so that reproducibility is markedly high.

EXAMPLE 3

Testing was performed as in Example 1 except that TP antigen was used as the antigen and a Treponemal antibody was measured. The experimentation was performed for 10 cases each to insure reproducibility.

The results showed that in the case of using sheep red blood cells agglutination sensitivity was equal to that in the case of using microcapsules but non-specific reaction was noted in 3 out of 10 cases; in the case of using the polystyrene latex, non-specific reaction was not noted but agglutination sensitivity was reduced to 1/16 that in the case of using microcapsules; no non specific reaction was noted in the case of using microcapsules.

As can be understood, using microcapsules as carrier particles provides high agglutination sensitivity due to the strong binding capability of the antigen to the microcapsules and there is no chance of any non-specific reaction due to the inherent absence of any antibody or antigen, unlike sheep red blood cells, so that reproducibility is markedly high.

Examples 4 through 6 below show that improved agglutination sensitivity is obtained by choosing suitable wall material for the microcapsules.

EXAMPLE 4

Into 25 g. of an oil mixture (specific gravity of about 1.10) of 11.8 g. of diisopropylnaphthalene and 13.2 g. of chlorinated parrafin (chlorination degree 50%), 0.1 g. of an ethylene diamine/propylene oxide addition product was dissolved. The solution was then ice-cooled. To this solution, 4 g. of a 50% methyl ethyl ketone solution of Desmodur-L (tradename, manufactured by Bayer A. G.: 1:4 addition product of tolylene diisocyanate and trimethylol propane) was dissolved. The resulting oily solution was poured into 65 g. of a 5% aqueous solution of polyvinyl alcohol (saponification degree, 88%; polymerization degree, 500) and the resulting mixture was emulsified with stirring. After the average dropet size reached about 7μ, the emulsion was diluted with 100 g. of water and the resulting mixture reacted at 75° C. for 1 hr. to microencapsulate the system.

The thus obtained polyurethane-wall microcapsules were washed with a phosphoric acid buffer. Thereafter, 0.5 g. of the thus washed microcapsules were dispersed in 5 ml. of fresh phosphoric acid buffer. To the dispersion, 1 ml. of egg albumin (25 mg/ml) was added as an antigen. After 100 μl of a 25% aqueous glutaraldehyde solution was further added to the dispersion, the mixture was reacted at room temperature for 1 hr. followed by centrifuging. The precipitate formed was washed with fresh phosphoric acid buffer and again, 0.5 g. each of the thus washed samples was dispersed into 5 ml. of fresh phosphoric acid buffer to obtain the buffer containing 1% of the antigen-bound microcapsules.

Thereafter, serial diluents of rabbit antisera up to $2^{12}(4096)$ times were prepared as in Example 1, and 25 μl of the antigen-bound microcapsules (diluted to a 1% concentration) was dropped on the anti-albumin diluents in 12 wells respectively on microplate as in Example 1. The microplate was thoroughly shaken to mix the antigen and anti-albumin and the system then allowed to stand at room temperature for about 3 hours.

Precipitation patterns were then observed and the minimum antibody concentration (antibody detection sensitivity) at which specific agglutination occurred determined. The results are shown in Table 1 below.

EXAMPLE 5

To 25 g. of a 10% aqueous solution of carboxy-modified polyvinyl alcohol (molecular weight 100,000, saponification degree 90%, carboxy group content: 5–6%), 2.5 g. of urea, 0.25 g. of resorcine and 0.3 g. of ammonium chloride were added. The mixture was stirred to dissolve all components. The pH of the resulting solution was then adjusted to 4.0 by adding a 0.1 N aqueous hydrochloric acid solution thereto. While vigorously stirring, 25 g. of the oil mixture having a specific gravity of 1.10 as used in Example 4 was emulsified in the above-described aqueous solution to prepare an O/W emulsion and the droplet size adjusted to a diameter of about 7μ as in Example 4, whereafter 6.4 g. of a 37% aqueous formaldehyde solution was added to the resulting emulsion. After the temperature of the system was adjusted to 60° C., encapsulation was conducted for 2 hrs. The polyurea-wall microcapsule liquid thus prepared was washed three times with fresh phosphoric acid buffer to remove remaining formalin, urea, protective colloid, etc.

Thereafter, antigen was bound to the microcapsules as in Example 1 and the detection sensitivity for antibody determined as per Example 1, the results are given in Table 1.

EXAMPLE 6

Polyurethane-urea wall-microcapsules were prepared as in Example 4 except that when the average drop size reached about 7μ, 100 g. of a 1% aqueous hexamethylene diamine solution was added instead of diluting with 100 g. of water.

The thus prepared polyurethane-urea wall microcapsules were washed three times with a phosphoric acid buffer as used in Example 1 and then antigen as in Example 1 was bound to the microcapsules as per Example 1 and the detection sensitivity of antibody was determined as per Example 1. The results are shown in Table 1.

TABLE 1

| Example No. | Wall Material | Detection Sensitivity* Antibody |
|---|---|---|
| 4 | polyurethane | $2^{11}$ |
| 5 | polyurea | $2^9$ |
| 6 | polyurethane-urea | $2^9$ |
| 1 | gelatin | $2^6$ |

*Detection sensitivity for antibody is expressed by the minimum antibody concentration at which the antigen-bound microcapsules cause agglutination. The minimum antibody concentration is obtained by mixing double serial diluents of the antibody with the antigen-bound microcapsule solution at a fixed concentration and observing the minimum concentration of the antibody at which agglutination occurs, and thus has no unit.

As will be understood from the results given above, antigen-bound microcapsules obtained using polyurethane walls, polyurea walls and polyurethane-urea walls selectively exhibit extremely high sensitivity detection for an antibody. Comparing this with the sensitivity for detecting an antibody in systems using gelatin wall capsules as obtained in Example 1, the sensitivity of the gelatin wall microcapsules is $2^6$, whereas the polyurea wall- and polyurethane-urea microcapsules provide a detection sensitivity 8 times that of the gelatin wall microcapsules, while the polyurethane microcapsules give a detection sensitivity 32 times that of the gelatin wall microcapsules.

The following examples 7 through 11 and comparison examples 1 through 3 demonstrate that microcapsules having selected specific gravity range improve the time period necessary for the analysis or judgement of an analytical results (hereafter simply referred to as judgement time).

EXAMPLE 7

To a 10% aqueous solution (25 g.) of a maleic anhydridemethyl vinyl ether copolymer (tradename "GANTREZ-AN 139", molecular weight, ca. 25,000, manufactured by General Aniline & Film Co., Ltd.), 2.5 g. of urea, 0.25 g. of resorcine and 0.3 g. of ammonium chloride were added. The mixture was then dissolved with stirring. The resulting solution was adjusted in pH to 4.0. An oil mixture of 11.8 g. of diisopropylnaphthalene and 13.2 g. of chlorinated parraffin (chlorine content, 50%) was emulsion-dispersed into the above aqueous solution to for an O/W emulsion. When an average droplet size became about 7μ, stirring was stopped. To the resulting emulsion, 6.7 g. of a 37% aqueous formaldehyde solution and 25 g. of water were added. After the temperature of the system was raised from ambient temperature to 65° C., reaction was continued for 2 hrs. The thus obtained microcapsules having a specific gravity of about 1.10 were washed three times with a phosphoric acid buffer having the same composition as used in Example 1 to remove remaining formalin, protective colloid, etc. 0.5 g. of the thus washed microcapsules was taken out and dispersed again in 5 ml. of the phosphoric acid buffer. To the dispersion, 1 ml. of an aqueous solution of ovalbumin (25 mg/ml) (manufactured by Biochemical Industry Co., Ltd.) was added as an antigen, and 100 μl of an aqueous glutalaldehyde solution was then added to mixture, whereafter, the mixture was reacted for 1 hr. at ambient temperature. After centrifuging, the system was washed with the phosphoric acid buffer and 0.5 g. of the washed microcapsules dispersed again in 5 ml. of the phosphoric acid buffer.

EXAMPLES 8-11 AND COMPARISON EXAMPLES 1-3

In a manner as in Example 7, microcapsules having various specific gravities and antigen-bound microcapsules using such microcapsules were prepared except that the composition of the core oil material (mixing ratio of diisopropylnaphthalene/chlorinated paraffin) was charged as indicated in Table 2 below. As Comparison Example 3, sheep red blood cells (specific gravity of about 1.10) were used as the carrier.

TABLE 2

| | Ex. 8 | Ex. 9 | Ex. 10 | Ex. 11 | Comp. Ex. 1 | Comp. Ex. 2 |
|---|---|---|---|---|---|---|
| diisopropyl-naphthalene (g) | 14.6 | 11.1 | 7.6 | 6.6 | 15.6 | 5.9 |
| chlorinated parrafin (g) | 10.4 | 13.9 | 17.4 | 18.4 | 9.4 | 19.1 |
| specific gravity | 1.07 | 1.11 | 1.15 | 1.16 | 1.06 | 1.17 |

Interpretation of Particulate Agglutination due to Antibody-Antigen Reaction Onto serial diluents of rabbit antibody (positive samples) and antibody-free serial diluents (negative samples) on a microplate, 25 μl of the thus prepared 1% antigen-bound microcapsules was dropped with a dropper, respectively, as per Example 1. The microplate was thoroughly shaken to mix and, while allowing to stand at room temperature, the time period until positive and/or negative patterns appeared as in Ex. 1 was measured.

Further, observation was made as to if the positive samples and negative samples properly caused agglutination and precipitation, respectively, in order to judge the same on a (+) or (−) scale. Then, the judgement ability was examined to determine whether the judgement on the positive and negative samples was clear or unclear.

The results obtained are summarized in Table 3 below.

TABLE 3

|  | Example No. | | | | | Comparison Example No. | | |
|---|---|---|---|---|---|---|---|---|
|  | 7 | 8 | 9 | 10 | 11 | 1 | 2 | 3 |
| specific gravity | 1.10 | 1.07 | 1.11 | 1.15 | 1.16 | 1.06 | 1.17 | 1.10 |
| judgement time (hr.) | ca. 2 | ca. 5 | ca. 1 | <1 | <1 | ca. 10 | impossible to interprete | ca. 4 |
| judgement ability | Δ | Δ | O | O | Δ | x | x | O |
| positive sample | + | + | ++ | ++ | + | + | − | ++ |
| negative sample | − | − | −− | −− | − | + | − | −− |
| total judgement | O | O | ⊚ | ⊚ | O | x | x | O |

In judgement ability,
O: (+) or (−) can easily be interpreted.
Δ: (+) or (−) difficult, but can be practically interpreted.
x: (+) or (−) cannot be interpreted.
(+)... Agglutination occurs.
(−)... Precipitation occurs.
In total judgement,
⊚: Detection efficiency is excellent.
O: Detection is possible.
x: Detection is impossible.

As will be understood from the results shown above, antigen-bound microcapsules having a specific gravity ranging from 1.07 to 1.16 had an excellent judgement time, although microcapsules having a specific gravity of 1.07 were somewhat inferior to sheep red blood cells; specifically, the judgement time using microcapsules having such a specific gravity range was short (approximately 1 to 2 hrs.).

In particular, microcapsules having a specific gravity ranging from 1.11 to 1.15 are preferred in that the detection capability thereof is comparable with sheep red blood cells and further the judgement time is very short.

In addition, the microcapsule carrier systems of the present invention do not cause undesired non-specific reaction and provide extremely high reproducibility. It is thus concluded, considering these results from an examination accuracy viewpoint, that the antigen- or antibody-bound microcapsules having a specific gravity ranging from 1.07 to 1.16 are superior, in detecting an antigen or antibody, to sheep red blood cells. Further, antigen- or antibody-bound microcapsules having a specific gravity ranging from 1.11 to 1.15 provide more improved detection.

The following examples 12 through 14 demonstrate the the microcapsule system of the present invention can be labelled with a marking substance to thereby enable one to quantitatively determin an antigen-antibody reaction.

EXAMPLE 12

To 25 g. of a 10% aqueous solution of a maleic anhydride-methyl vinyl ether copolymer(GANTREZ-AN 139, molecular weight, ca. 25,000, manufactured by General Aniline & Film Co., Ltd.), 2.5 g. of urea, 0.25 g. of resorcine and 0.3 g. of ammonium chloride were added. The resulting mixture was mixed to dissolve all components. To the the obtained aqueous solution, 26 g. of a mixture of 1.0 g. of White Flour Blue (tradename, manufactured by Sumitomo Chemical Co., Ltd. CI Fluorescent Brightening Agent 91 described in Senryo Binran (Handbook of Dye), published Maruzen Co., Ltd., Tokyo, 1974) as a marking substance, 11.8 g. of diisopropylnaphthalene and 13.2 g. of chlorinated parrafin (chlorine content 50%) was added. The mixture was emulsified until the average dropet size reached 6μ. Then, 6.4 g. of a 37% formaldehyde aqueous solution was added to the system and the mixture heated at 60° C. for 2 hrs. The thus formed microcapsules were washed twice with water and 1.0 g. of the washed microcapsules was taken and suspended in 10 ml. of a phosphoric acid buffer having the same composition as used in Example 1. Subsequently, 100 μl of a 25% glutaraldehyde aqueous solution was mixed with the suspension and the mixture then reacted at 25° C. for 1 h. After centrifuging, the system was washed with the phosphoric acid buffer.

Separately, 0.95 ml. of physiological saline solution was added to 0.05 ml. of anti-human IgG (28 mg/ml) to prepare a solution mixture. The solution mixture was mixed with 2 ml. (0.25% concentration) of the glutaraldehyde-treated microcapsules described above and the resulting mixture incubated at 37° C. for 1 hour and thereafter allowed to stand in a refrigerator overnight.

After the system was washed twice with a 0.2% glycine-containing physiological saline solution, the phosphoric acid buffer further containing 1 ml. of 3% BSA was added to the system. A reagent comprising microcapsules having bound thereto anti-human IgG was thus obtained.

In order to determine a Treponemal antibody in blood, TP antigen (Treponema pallidum (Nicholas strain)) was pulverized with an electric wave of 25 kHz. This antigen was coated onto a glass plate, and dried and then immobilized with acetone. On the coated area, 25 μl of diluted serum was dropped and the reaction was performed at 37° C. for 1 hr. After washing with the phosphoric acid buffer, the above-described reagent was added to the reaction mixture, and the reaction was performed at 37° C. for a further 1 hr. Fluorescent intensity was measured using a fluorometer. Thus, the pallidum antigen could easily be determined accurately.

EXAMPLE 13

Microcapsules were obtained as in Example 12, diisopropylnaphthalene and chlorinated parrafin as per Example 12 being used as the core material in combination with CI Fluorescent Brightening Agent 91 with $Fe_2O_3$ also being present. After the microcapsules were treated with glutaraldehyde as in Example 12, an anti-α-fetoprotein was bound thereto to obtain a microcapsule carrier. The thus obtained microcapsule carrier was employed as a solid phase carrier in the conventional enzyme immunology sandwich method and the amount of α-fetoprotein in serum was determined. this system, the carrier was easily separated from a solution phase and measurement procedure was markedly simplified and reproducibility, as well as stability, were also improved, as compared as a prior art system where glass beads were employed as a carrier.

EXAMPLE 14

Microcapsules were prepared as in Example 12 except that 2-hydroxy-4-methoxybenzophenone was used as the core material. After treating with glutaraldehyde as in Example 12, an anti-HCG was bound thereto and the amount of HCG in a sample could be detected by UV absorption at 280 to 340 nm in a simple manner.

EXAMPLE 15

Microcapsules having a specific gravity of 0.80 were prepared as in Example 7 except that 18.0 g. of isoparaffin containing 1% of an oleophilic blue dye O-79 (CI Solvent Blue 55, *Senryo Binran*(Handbook of Dye), Maruzen Co., Ltd., 1974) was employed as a core material.

Egg albumin was bound to the thus obtained microcapsules as in Example 7.

25 μl of the thus prepared 1% antigen-bound microcapsules was dropped onto whole blood serial diluents containing rabbit antibody (positive samples) and antibody-free whole blood serial diluents (negative samples) on a microplate with a dropper. The microplate was well shaken to mix. After standing for 10 mins. at ambient temperature, blood cells were precipitated and the microcapsules floated on the surface of the supernatant serum phase where, the presence or absence of agglutination could be interpreted by the eye or microscopically. Interpretation was very easy because of the colored microcapsules and their capability to float up due to their low specific gravity which also permitted their use with whole blood.

To prevent blood coagulation, heparin was incorporated into the whole blood as an anti-coagulant.

While the invention has been described in detail and with reference to specific embodiments thereof, it will be apparent to one skilled in the art that various changes and modifications can be made therein without departing from the spirit and scope thereof.

We claim:

1. A microcapsule comprising an oily liquid core material and a wall material having bound thereto an antigen or antibody to the surface thereof, wherein a marking substance is incorporated into said core material.

2. The microcapsule of claim 1 wherein the specific gravity thereof is between about 0.8 and about 1.20.

3. The microcapsule of claim 2 wherein said specific gravity is between 1.05 and 1.20.

4. The microcapsule of claim 3 wherein said specific gravity is between 1.07 and 1.16.

5. The microcapsule of claim 1 wherein said marking substance is selected from the group consisting of an isotope, an enzyme, a fluorescent substance, a UV absorbent and a dye.

6. The microcapsule of claim 5 wherein said isotope is selected from the group consisting of $^{125}I$, $^{131}I$, $^3H$ and $^{14}C$.

7. The microcapsule of claim 5 wherein said enzyme is selected from the group consisting of alkali phosphatase, β-galactosidase, acetylcholine esterase, glucoamylase, maleic acid dehydrogenase glucose-6-phosphoric acid dehydrogenase, peroxidase and glutaroxidase.

8. The microcapsule of claim 5 wherein said fluorescent substance is selected from the group consisting of stilbene and derivatives thereof, coumarine derivatives, pyrazoline derivatives, 9. The microcapsule of claim 5 wherein said UV absorbent is selected from the group consisting of salicylic acid derivatives, benzophenone derivatives and benzotriazole derivatives.

10. A method for determining a biological component having immunological activity which comprises mixing a microcapsule comprising an oily liquid core material and a wall material having bound thereto an antigen or antibody at the surface thereof with said biological component to thereby cause an immunological reaction therebetween, wherein a marking substance is incorporated into said core material.

11. The method for determining a biological component of claim 10 wherein said microcapsules have a specific gravity between 0.8 and 1.20.

12. The microcapsule of claim 1 wherein said wall material is gelatin.

13. The microcapsule of claim 1 wherein said oily liquid substance is selected from the group consisting of a natural mineral oil, an animal oil, a plant oil and a synthetic oil.

14. The microcapsule of claim 1 wherein said wall material is selected from the group consisting of polyurethane, polyurea, polyurethane-urea, melamine and gelatin.

15. The microcapsule of claim 10 wherein said wall material is selected from the group consisting of a polyurethane, a polyurea and a polyurethane-urea.

16. The microcapsule of claim 6 wherein said marking substance is selected from the group consisting of a fluorescent substance, a UV absorbent and a dye.

17. The microcapsule of claim 16 wherein said marking substance is said dye.

18. The microcapsule of claim 1 capable of effecting an agglutination reaction.

19. The microcapsule of claim 1 wherein said antigens or antibodies are bound to said surface by cross-linking, covalent binding or coupling.

20. The microcapsule of claim 1 wherein said antigen or antibody is bound to said surface via an aldehyde.

21. The microcapsule of claim 20 wherein said surface contains amino, imino or hydroxy groups.

22. The microcapsule of claim 1 wherein said wall material is substantially impermeable.

23. The method of claim 11 wherein said oily substance is an oil selected from the group consisting of a natural mineral oil, an animal oil, a plant oil and a synthetic oil.

24. The method of claim 10 wherein said wall material is selected from the group consisting of polyurethane, polyurea, polyurethane-urea, melamine and gelatin.

25. The method for determining a biological component of claim 24 wherein said microcapsule wall is composed of a member selected from the group consisting of a polyurethane, a polyurea and a polyurethane-urea.

26. The method of claim 10 wherein said marking substance is selected from the group consisting of a fluorescent substance, an UV absorbent and a dye.

27. The method of claim 26 wherein said marking substance is said dye.

28. The method of claim 10 wherein said immunological reaction is an agglutination reaction.

29. The method of claim 10 wherein said antigen or antibody is bound to said wall material by cross-linking, covalent bonding or coupling.

30. The method of claim 10 wherein said antigen or antibody is bound to said wall material via an aldehyde.

31. The method of claim 30 wherein said wall material contains amino, imino or hydroxy groups.

32. The method of claim 10 wherein said wall material is substantially impermeable.

33. The method of claim 10 wherein said marking substance is incorporated into said core material.

34. The microcapsule of claim 1 wherein said marking substance is a magnetic substance.

35. The microcapsule of claim 34 wherein said magnetic substance is selected from the group consisting of iron powders, nickel, cobalt, $CrO_2$, CoO, NiO, $Mn_2O_3$, a magnetic zinc oxide, a magnetic iron oxide, an alloy of Al, Ni, Co or Cu, chalcogenides and ferricolloid powders.

36. The microcapsule of claim 1 wherein said wall material is a protein or a resin.

37. The method of claim 10 wherein said wall material is a protein or a resin.

* * * * *